United States Patent
Sakaguchi et al.

(10) Patent No.: US 9,931,090 B2
(45) Date of Patent: Apr. 3, 2018

(54) IMAGE PROCESSING APPARATUS, X-RAY DIAGNOSIS APPARATUS, AND DISPLAY METHOD

(71) Applicant: Toshiba Medical Systems Corporation, Otawara-shi (JP)

(72) Inventors: Takuya Sakaguchi, Utsunomiya (JP); Ko Fuchigami, Otawara (JP); Shinichi Hashimoto, Otawara (JP); Hiroyuki Ohuchi, Otawara (JP)

(73) Assignee: Toshiba Medical Systens Corporation, Otawara-shi (JP)

( * ) Notice: Subject to any disclaimer, the term of this patent is extended or adjusted under 35 U.S.C. 154(b) by 60 days.

(21) Appl. No.: 14/642,808

(22) Filed: Mar. 10, 2015

(65) Prior Publication Data

US 2015/0173698 A1 Jun. 25, 2015

Related U.S. Application Data

(63) Continuation of application No. PCT/JP2013/075572, filed on Sep. 20, 2013.

(30) Foreign Application Priority Data

Sep. 20, 2012 (JP) ................. 2012-207496

(51) Int. Cl.
*A61B 6/00* (2006.01)
*A61B 6/12* (2006.01)
(Continued)

(52) U.S. Cl.
CPC ............. *A61B 6/463* (2013.01); *A61B 6/12* (2013.01); *A61B 6/466* (2013.01); *A61B 6/503* (2013.01);
(Continued)

(58) Field of Classification Search
CPC ...... A61B 6/463; A61B 6/5247; A61B 6/5261
See application file for complete search history.

(56) References Cited

U.S. PATENT DOCUMENTS

2009/0043200 A1 2/2009 Abe
2009/0118614 A1* 5/2009 Sendai ................ A61B 5/0077
600/437
(Continued)

FOREIGN PATENT DOCUMENTS

EP 2 160 978 A1 3/2010
JP 2009-039429 A 2/2009
(Continued)

OTHER PUBLICATIONS

International Search Report dated Oct. 22, 2013 for PCT/JP2013/075572 filed on Sep. 20, 2013 with English Translation.
Written Opinion dated Oct. 22, 2013 for PCT/JP2013/075572 filed on Sep. 20, 2013.
Chinese Office Action dated Oct. 28, 2016 in Chinese Patent Application No. 2013-80049235.3.
Combined Office Action and Search Report dated Oct. 28, 2016 in Chinese Patent Application No. 201380049235.3 (with English translation of categories of cited documents).

*Primary Examiner* — Dani Fox
(74) *Attorney, Agent, or Firm* — Oblon, McClelland, Maier & Neustadt, L.L.P.

(57) ABSTRACT

An image processing apparatus according to an embodiment includes a determination unit and a display control unit. The determination unit that determines whether an X-ray image serving as a first image is to be displayed as a moving image or a still image and a second image is to be displayed as a moving image or a still image according to display states of the images. The display control unit that controls a display unit to display thereon at least any one of superimposed images of a combination of a moving image and a moving image, a combination of a moving image and a still image, and a combination of a still image and a moving image of the X-ray image and the second image, according to the determination made by the determination unit.

10 Claims, 13 Drawing Sheets

(51) Int. Cl.
*A61B 8/08* (2006.01)
*A61B 8/00* (2006.01)
*G06T 11/60* (2006.01)

(52) U.S. Cl.
CPC .......... *A61B 6/5205* (2013.01); *A61B 6/5217* (2013.01); *A61B 6/5247* (2013.01); *A61B 6/5264* (2013.01); *A61B 6/5288* (2013.01); *A61B 8/0883* (2013.01); *A61B 8/463* (2013.01); *A61B 8/466* (2013.01); *A61B 8/5261* (2013.01); *G06T 11/60* (2013.01); *A61B 8/4263* (2013.01); *A61B 8/485* (2013.01); *A61B 8/488* (2013.01); *G06T 2207/10016* (2013.01); *G06T 2207/10116* (2013.01)

(56) References Cited

U.S. PATENT DOCUMENTS

| | | | |
|---|---|---|---|
| 2009/0175418 A1 | 7/2009 | Sakurai et al. | |
| 2011/0270123 A1* | 11/2011 | Reiner | A61B 6/463 600/558 |
| 2011/0282206 A1* | 11/2011 | Ichioka | A61B 8/463 600/443 |
| 2014/0039303 A1* | 2/2014 | Kanzaki | A61B 6/12 600/424 |

FOREIGN PATENT DOCUMENTS

| | | |
|---|---|---|
| JP | 2009-160307 A | 7/2009 |
| JP | 2009-247739 A | 10/2009 |
| JP | 2012-045285 A | 3/2012 |

* cited by examiner

FIG.8

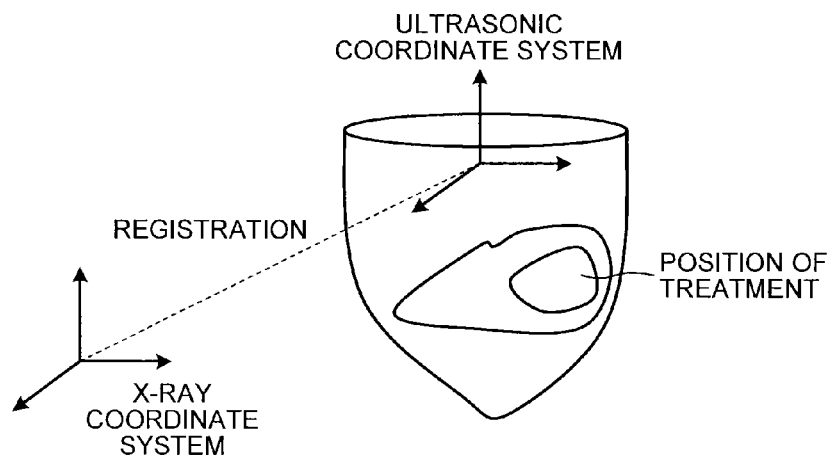

FIG.9

| ULTRASONIC IMAGE | X-RAY IMAGE |
|---|---|
| STILL IMAGE (PLUS FRAME-BY-FRAME PLAYBACK) | STILL IMAGE (CONTRAST IMAGE) |
| MOVING IMAGE | STILL IMAGE (CONTRAST IMAGE) |
| STILL IMAGE (AI) | MOVING IMAGE (FLUOROSCOPY OR RM) |
| MOVING IMAGE (HEART RATE MOTION, ELECTRICAL CONDUCTION) | MOVING IMAGE (FLUOROSCOPY OR RM) |
| MOVING IMAGE (HEART RATE MOTION ONLY) | MOVING IMAGE (FLUOROSCOPY OR RM) |
| MOVING IMAGE (ELECTRICAL CONDUCTION ONLY) | MOVING IMAGE (FLUOROSCOPY OR RM) |
| MOVING IMAGE (ANOTHER WINDOW) | MOVING IMAGE (FLUOROSCOPY OR RM) |

IMAGE PROCESSING APPARATUS, X-RAY DIAGNOSIS APPARATUS, AND DISPLAY METHOD

CROSS-REFERENCE TO RELATED APPLICATIONS

This application is a continuation of International Application No. PCT/JP2013/075572, filed on Sep. 20, 2013 which claims the benefit of priority of the prior Japanese Patent Application No. 2012-207496, filed on Sep. 20, 2012, the entire contents of which are incorporated herein by reference.

FIELD

Embodiments described herein relate generally to an image processing apparatus, an X-ray diagnosis apparatus, and a display method.

BACKGROUND

Conventionally, the cardiac resynchronization therapy (CRT) has been known as an example of heart failure treatment. This therapy is used for treatment of a disease in which abnormality of the impulse conduction system of the heart leads to a wrong timing of motion of the cardiac muscle surrounding a ventricle, so that core-walls of the right and left ventricles do not move at the same time, and the ventricles do not contract at the correct timing, thus causing insufficient cardiac output of the blood, for example.

In the CRT, an electrode is placed in the part where the heart hardly moves (the site of latest activation) so that the ventricles of the heart contract in a synchronized manner. Specifically, in the CRT, the site of latest activation is determined through strain analysis by using an ultrasound diagnosis apparatus, and the electrode is placed on the closest vein to the site of latest activation with reference to the X-ray image radiographed by an X-ray diagnosis apparatus.

The electrode placed as described above applies stimuli electric potential at a proper timing, whereby the cardiac muscle contracts at a proper timing and controls the motion of the ventricles. In the conventional technology, however, a superimposed image of an X-ray image and another medical image can be hardly displayed with high visibility.

BRIEF DESCRIPTION OF THE DRAWINGS

FIG. 8 is a diagram for explaining an example of processing performed by a positioning unit 151 according to the first embodiment;

FIG. 9 is a diagram illustrating an example of combinations of images used for a fused image determined by a determination unit according to the first embodiment;

DETAILED DESCRIPTION

According to embodiment, an image processing apparatus comprising a determination unit and a display control unit. The determination unit that determines whether an X-ray image serving as a first image is to be displayed as a moving image or a still image and a second image is to be displayed as a moving image or a still image according to display states of the images. The display control unit that controls a display unit to display thereon at least any one of superimposed images of a combination of a moving image and a moving image, a combination of a moving image and a still image, and a combination of a still image and a moving image of the X-ray image and the second image, according to the determination made by the determination unit.

Figure 1:
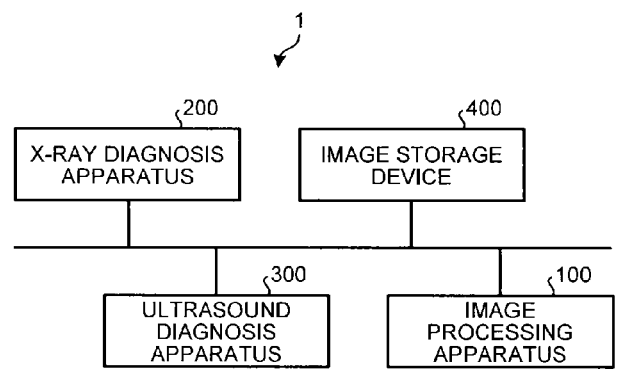
FIG. 1 is a diagram illustrating an example of the configuration of an image processing system according to a first embodiment.

Hereinafter, embodiments of an image processing apparatus according to the present application are described in detail below. In a first embodiment, an image processing system including an image processing apparatus according to the present application is described as an example. FIG. 1 is a diagram illustrating an example of the configuration of an image processing system according to a first embodiment. In the description in the embodiment, an ultrasonic image is used for a medical image superimposed onto an X-ray image, however, the embodiment is not limited to this example.

As illustrated in FIG. 1, an image processing system 1 according to the first embodiment includes an image processing apparatus 100, an X-ray diagnosis apparatus 200, an ultrasound diagnosis apparatus 300, and an image storage device 400. The apparatuses illustrated in FIG. 1 are in a communicable state directly or indirectly to each other through a local area network (LAN) provided in a hospital, for example. When a picture archiving and communication system (PACS) is implemented in the image processing system 1, the apparatuses transmit and receive medical images to and from each other according to the digital imaging and communications in medicine (DICOM) standard.

In the image processing system 1, the X-ray diagnosis apparatus 200 acquires X-ray images according to the operations of the engineer (operator) of the apparatus and the ultrasound diagnosis apparatus 300 acquires ultrasonic images according to the operations of the engineer (operator) of the apparatus. The image processing apparatus 100 then displays the ultrasonic image appropriately aligned with the X-ray image. This enables a doctor to place an electrode on a placing position planned using the ultrasound diagnosis apparatus in a precise manner while performing the cardiac resynchronization therapy (CRT).

The image storage device 400 is a database that stores medical images. Specifically, the image storage device 400 according to the first embodiment records X-ray images transmitted from the X-ray diagnosis apparatus 200 and ultrasonic images transmitted from the ultrasound diagnosis apparatus 300 in a storage unit and stores the images therein. That is, the image processing apparatus 100 according to the first embodiment may receive the image data directly from the X-ray diagnosis apparatus 200 or the ultrasound diagnosis apparatus 300, and may acquire the images temporarily stored in the image storage device 400.

Figure 2:
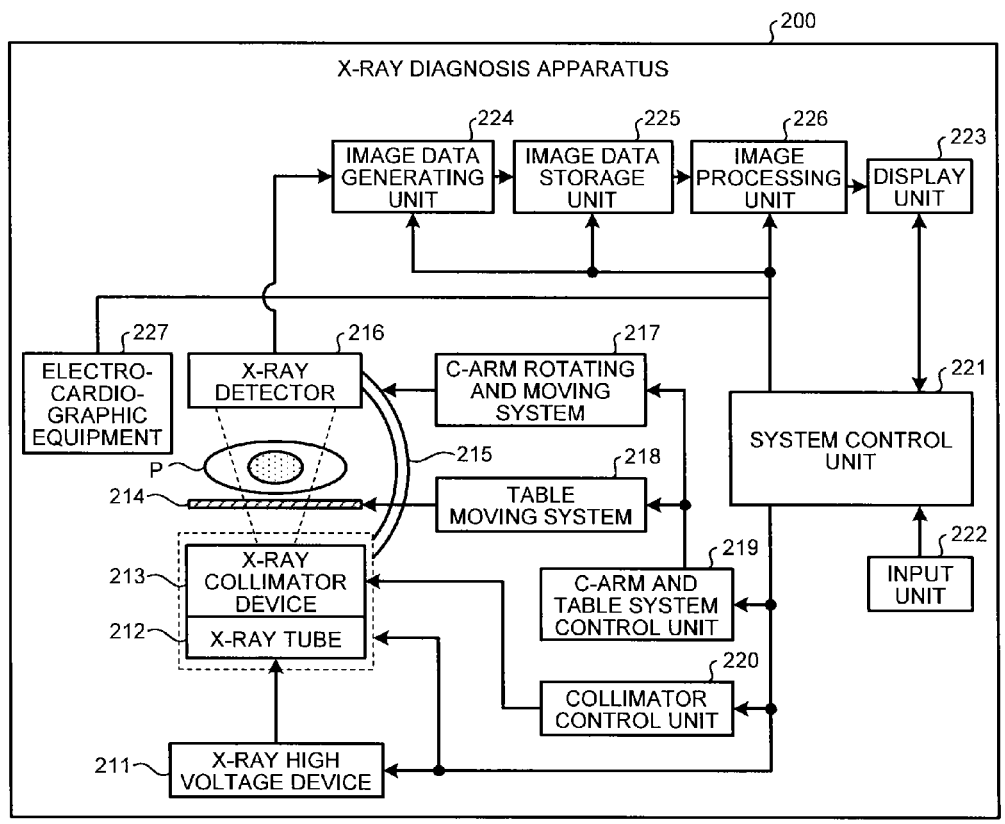
FIG. 2 is a diagram illustrating an example of the configuration of an X-ray diagnosis apparatus according to the first embodiment.

Firstly, the following describes the configuration of the X-ray diagnosis apparatus 200 according to the first embodiment. FIG. 2 is a diagram illustrating an example of the configuration of the X-ray diagnosis apparatus 200 according to the first embodiment. As illustrated in FIG. 2, the X-ray diagnosis apparatus 200 according to the first embodiment includes an X-ray high voltage device 211, an X-ray tube 212, an X-ray collimator device 213, a table 214, a C-arm 215, and an X-ray detector 216. The X-ray diagnosis apparatus 200 according to the first embodiment also includes a C-arm rotating and moving system 217, a table moving system 218, a C-arm and table system control unit 219, a collimator control unit 220, a system control unit 221, an input unit 222, and a display unit 223. Furthermore, the X-ray diagnosis apparatus 200 according to the first embodiment includes an image data generating unit 224, an image data storage unit 225, an image processing unit 226, and electrocardiographic equipment 227.

The X-ray high voltage device 211 generates a high voltage under the control of the system control unit 221 and supplies the generated high voltage to the X-ray tube 212. The X-ray tube 212 generates X-rays using the high voltage supplied from the X-ray high voltage device 211.

The X-ray collimator device 213 narrows down the X-rays generated by the X-ray tube 212 under the control of the collimator control unit 220 so that the region of interest of a subject P is selectively irradiated with the X-rays. For example, the X-ray collimator device 213 includes four slidable collimator blades. The X-ray collimator device 213 slides the collimator blades under the control of the collimator control unit 220, thereby narrowing down the X-rays generated by the X-ray tube 212 so that the subject P is irradiated with the X-rays. The table 214 is a bed for mounting the subject P and disposed on a not-illustrated couch. The subject P is not included in the X-ray diagnosis apparatus 200.

The X-ray detector 216 detects the X-rays transmitted through the subject P. For example, the X-ray detector 216 includes detecting elements arranged in a matrix shape. Each of the detecting elements converts the X-ray transmitted through the subject P into the electrical signals, accumulates them, and transmits the accumulated electrical signals to the image data generating unit 224.

The C-arm 215 retains the X-ray tube 212, the X-ray collimator device 213, and the X-ray detector 216. The X-ray tube 212 and the X-ray collimator device 213 are disposed on an opposite side of the X-ray detector 216 across the subject P and supported by the C-arm 215.

The C-arm rotating and moving system 217 is a system for rotating and moving the C-arm 215. The table moving system 218 is a system for moving the table 214. The C-arm and table system control unit 219 controls the C-arm rotating and moving system 217 and the table moving system 218 under the control of the system control unit 221, thereby adjusting the rotation and movement of the C-arm 215, and the movement of the table 214. The collimator control unit 220 adjusts the degree of opening of the collimator blades included in the X-ray collimator device 213 under the control of the system control unit 221, thereby controlling the radiation range of the X-rays with which the subject P is irradiated.

The electrocardiographic equipment 227 acquires an electrocardiogram (ECG) of the subject P to which not-illustrated terminals are attached. The electrocardiographic equipment 227 then transmits the acquired electrocardiogram together with time information to the image data generating unit 224 and the image processing unit 226.

The image data generating unit 224 generates an X-ray image using the electrical signals converted by the X-ray detector 216 from the X-rays, and stores the generated X-ray image in the image data storage unit 225. For example, the image data generating unit 224 performs various types of processing such as current-voltage conversion, analog-digital (A/D) conversion, and parallel-serial conversion on the electrical signals received from the X-ray detector 216, thereby generating the X-ray image.

More specifically, the image data generating unit 224 radiographs along time series the heart of the subject P into which a contrast material has been injected, thereby generating a plurality of X-ray images. The image data generating unit 224 stores the generated X-ray images in the image data storage unit 225. Specifically, the image data generating unit 224 according to the present embodiment associates the generated X-ray images with the electrocardiogram received from the electrocardiographic equipment 227 and the time information and stores them in the image data storage unit 225.

The image data storage unit 225 stores therein the X-ray images generated by the image data generating unit 224. For example, the image data storage unit 225 associates the X-ray images generated by the image data generating unit 224 with the radiography time and the electrocardiogram during the radiography time and stores them. The image processing unit 226 performs various types of image processing on the image data stored in the image data storage unit 225. For example, the image processing unit 226 processes a plurality of X-ray images radiographed along time series and stored in the image data storage unit 225, thereby generating a moving image.

The input unit 222 receives various types of instructions from an operator such as a doctor and an engineer who operates the X-ray diagnosis apparatus 200. For example, the input unit 222 includes a mouse, a keyboard, a button, a trackball, and a joystick, for example. The input unit 222 transfers the instruction received from the operator to the system control unit 221. For example, the input unit 222 receives an instruction for turning the power of the X-ray diagnosis apparatus 200 ON.

The display unit 223 displays a graphical user interface (GUI) for receiving instructions by the operator, and image data stored in the image data storage unit 225. For example, the display unit 223 includes a monitor. The display unit 223 may include a plurality of monitors.

The system control unit 221 controls the overall operations of the X-ray diagnosis apparatus 200. For example, the system control unit 221 controls the X-ray high voltage device 211 according to the operator's instruction forwarded from the input unit 222 to adjust the voltage supplied to the X-ray tube 212, thereby controlling the amount of X-rays or turning ON and OFF of X-rays with which the subject P is irradiated. For another example, the system control unit 221 controls the C-arm and table system control unit 219 according to the operator's instruction to adjust the rotation and movement of the C-arm 215, and the movement of the table 214. For still another example, the system control unit 221 controls the collimator control unit 220 according to the operator's instruction by an operator to adjust the degree of opening of the collimator blades included in the X-ray collimator device 213, thereby controlling the radiation range of the X-rays with which the subject P is irradiated.

The system control unit 221 controls image data generating processing performed by the image data generating unit 224, image processing performed by the image processing unit 226, or analysis processing according to the operator's instruction by an operator. The system control unit 221 performs control for displaying on the monitor or monitors of the display unit 223 a graphical user interface (GUI) for receiving instructions by the operator and images stored in the image data storage unit 225.

Figure 3:
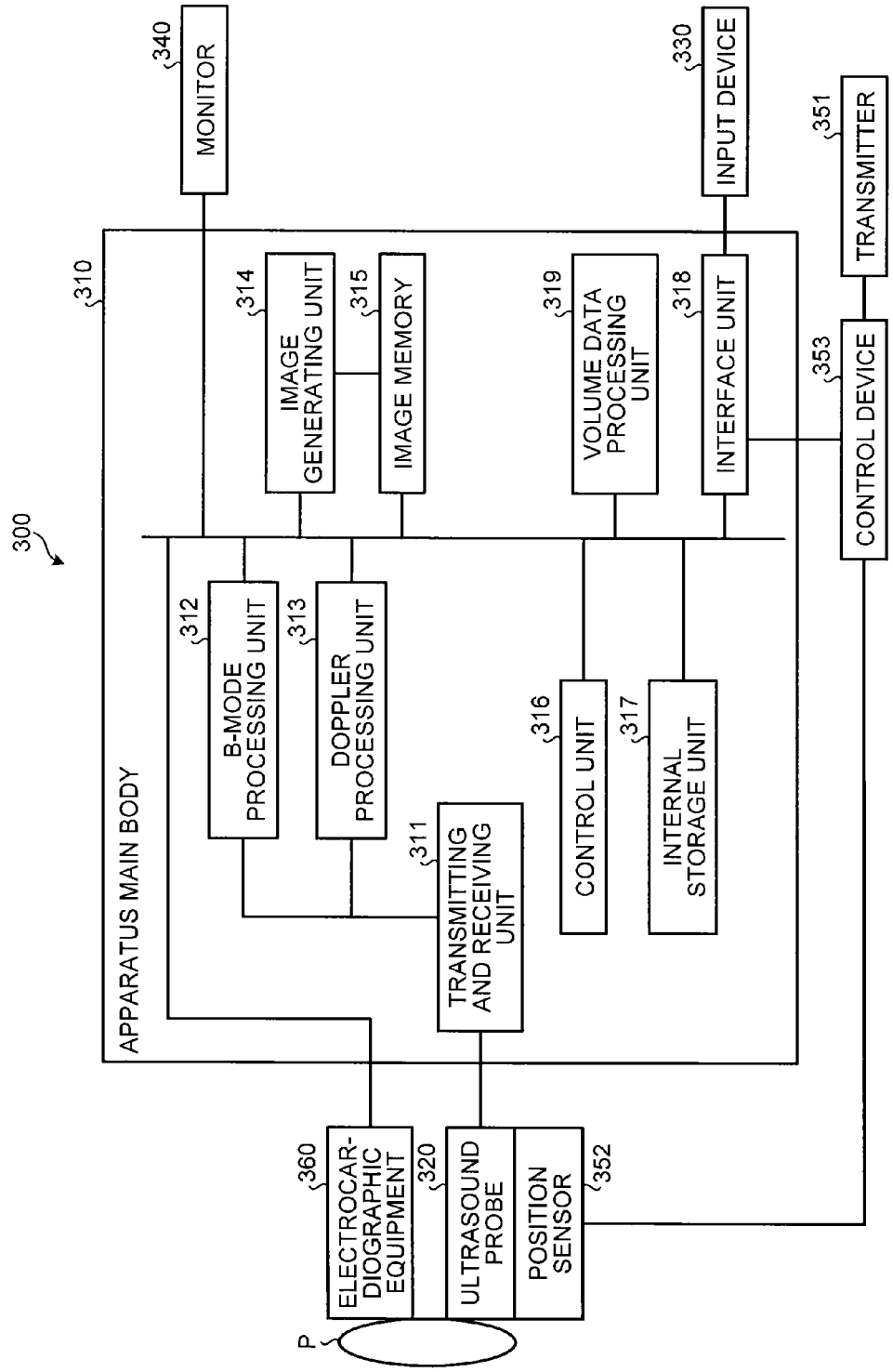
FIG. 3 is a diagram illustrating an example of the configuration of an ultrasound diagnosis apparatus according to the first embodiment.

The following describes the configuration of the ultrasound diagnosis apparatus according to the first embodiment with reference to FIG. 3. FIG. 3 is a diagram for explaining the configuration of the ultrasound diagnosis apparatus 300 according to the first embodiment. As illustrated in FIG. 3, the ultrasound diagnosis apparatus 300 according to the first embodiment includes an apparatus main body 310, an ultrasound probe 320, an input device 330, a monitor 340, a transmitter 351, a position sensor 352, a control device 353, and electrocardiographic equipment 360.

The ultrasound probe 320 includes a plurality of piezoelectric transducer elements that generate ultrasound based on driving signals supplied from a transmitting and receiving unit 311 included in the apparatus main body 310, which will be described later. In addition, the ultrasound probe 320 receives a reflected wave from the subject P and converts it into electrical signals. The ultrasound probe 320 includes a matching layer provided for the piezoelectric transducer elements, and a backing material that prevents the ultrasound of piezoelectric transducer elements from being transmitted backward. For example, the ultrasound probe 320 is a sector ultrasound probe, a linear ultrasound probe, or a convex ultrasound probe.

When the ultrasonic wave is transmitted from the ultrasound probe 320 to the subject P, the transmitted ultrasonic wave is sequentially reflected on discontinuity surfaces of acoustic impedance in internal body tissues of the subject P, and received by a plurality of piezoelectric transducer elements included in the ultrasound probe 320 as reflected wave signals. The amplitude of the received reflected wave signals depends on the difference of the acoustic impedance on the surfaces of discontinuity where the ultrasonic wave is reflected. It should be noted that the reflected wave signals obtained when the transmitted ultrasound pulse is reflected on the surfaces of a moving bloodstream or a moving cardiac wall (i.e., moving object) receives frequency shift depending on the velocity component with respect to the ultrasound transmission direction of the moving object due to the Doppler effect.

In the present embodiment, the subject P is scanned in three dimensions by the ultrasound probe 320. The ultrasound probe 320 may mechanically swing and move a plurality of piezoelectric transducer elements of a one-dimensional ultrasound probe. The ultrasound probe 320 may be a two-dimensional ultrasound probe having a plurality of piezoelectric transducer elements arranged in two dimensions in a matrix shape.

The input device 330 includes a trackball, a switch, a button, and a touch command screen and receives various types of setting demands from an operator of the ultrasound diagnosis apparatus 300. The input device 330 then transfers the received various types of setting demands forward to the apparatus main body 310. For example, the input device 330 receives various types of operations relating to alignment of an ultrasonic image and an X-ray image.

The monitor 340 displays a graphical user interface (GUI) used for inputting various types of setting demands by the operator of the ultrasound diagnosis apparatus 300 using the input device 330. The monitor 340 also displays side by side an ultrasonic image and an X-ray computed tomography (CT) image generated in the apparatus main body 310.

The transmitter 351 transmits a reference signal. Specifically, the transmitter 351 is disposed in an arbitrary position and forms a magnetic field outward with itself as the center of the magnetic field. The position sensor 352 receives the reference signal, thereby acquiring the positional information in the three-dimensional space. Specifically, the position sensor 352 is mounted on the surface of the ultrasound probe 320 and detects the three-dimensional magnetic field formed by the transmitter 351. The position sensor 352 then converts information of the detected magnetic field into signals and outputs the signals to the control device 353.

The control device 353 calculates the coordinates and the orientation of the position sensor 352 in the space having the transmitter 351 as its origin based on the signals received from the position sensor 352. The control device 353 then outputs the calculated coordinates and orientation to a control unit 316 of the apparatus main body 310. It should be noted that the diagnosis of the subject P is performed in the magnetic field area where the position sensor 352 mounted on the ultrasound probe 320 can precisely detect the magnetic field of the transmitter 351. In the embodiment, a magnetic sensor is used as a sensor that acquires positional information, however, the embodiment is not limited to this example. An infrared sensor, an optical sensor, or a camera may be used instead of the magnetic sensor.

The electrocardiographic equipment 360 is coupled to the apparatus main body 310 and acquires an electrocardiogram (ECG) of the subject P on which ultrasound scanning is performed. The electrocardiographic equipment 360 transmits the acquired electrocardiogram and time information to the apparatus main body 310.

The apparatus main body 310 is an apparatus that generates ultrasonic images based on the reflected wave received by the ultrasound probe 320. As illustrated in FIG. 3, the apparatus main body 310 includes a transmitting and receiving unit 311, a B-mode processing unit 312, a Doppler processing unit 313, an image generating unit 314, an image memory 315, a control unit 316, an internal storage unit 317, an interface unit 318, and a volume data processing unit 319.

The transmitting and receiving unit 311 includes a trigger generating circuit, a delay circuit, and a pulser circuit, and supplies driving signals to the ultrasound probe 320. The pulser circuit repeatedly generates rate pulses for forming ultrasonic waves to be transmitted at a predetermined rate frequency. The delay circuit supplies a delay time necessary to converge the ultrasonic waves generated from the ultrasound probe 320 into a beam for each of the piezoelectric transducer elements and to determine the transmission directionality, to each of rate pulses generated by the pulser circuit. The trigger generating circuit applies driving pulses to the ultrasound probe 320 at a timing based on the rate pulses. That is, the delay circuit changes the delay time supplied to each of the rate pulses, thereby arbitrarily adjusting the transmission direction from the surface of the piezoelectric transducer elements.

The transmitting and receiving unit 311 includes an amplifier circuit, an A/D converter, and an adder. The transmitting and receiving unit 311 performs various types of processing on the reflected wave signals received by the ultrasound probe 320 and generates reflected wave data. The amplifier circuit amplifies the reflected wave signals for each channel and performs gain correction processing. The A/D converter supplies a delay time necessary to perform A/D-conversion on the reflected wave signals on which gain correction has been performed and to determine transmission directionality. The adder performs addition processing on the reflected wave signals processed by the A/D converter, thereby generating the reflected wave data. The addition processing performed by the adder enhances a reflect component from the direction corresponding to the reception directionality of the reflected wave signals.

As described above, the transmitting and receiving unit 311 controls the transmission directivity and the reception directionality in transmitting and receiving ultrasound. The transmitting and receiving unit 311 has a function capable of instantly change delay information, a transmission frequency, a transmission drive voltage, the number of aperture elements under the control of the control unit 316, which will be described later. In particular, changes in the transmission drive voltage can be achieved with, a linear amplifier oscillation circuit capable of instantly changing a value, or a mechanism for electrically changing a plurality of power units. The transmitting and receiving unit 311 is capable of transmitting and receiving different waveforms for each frame or each rate.

The B-mode processing unit 312 receives from the transmitting and receiving unit 311, the reflected wave data that is the processed reflected wave signals on which gain correction processing, A/D conversion processing, and addition processing have been performed. The B-mode processing unit 312 then performs logarithm amplification and envelope detection processing, for example, on the received data, thereby generating data in which the signal intensity is represented with the level of brightness (B-mode data).

The Doppler processing unit 313 performs frequency analysis of the speed information using the reflected wave data received from the transmitting and receiving unit 311. The Doppler processing unit 313 then extracts a bloodstream echo component, a tissue echo component, and a contrast material echo component due to the Doppler effect and generates data in which the moving object information such as the average speed, distribution, and power is extracted at multiple points (Doppler data).

The image generating unit 314 generates ultrasonic images from the B-mode data generated by the B-mode processing unit 312 and the Doppler data generated by the Doppler processing unit 313. Specifically, the image generating unit 314 converts scanning line signal arrays of the ultrasound scanning into scanning line signal arrays in a video format typically used in televisions (scan conversion), thereby generating ultrasonic images (e.g., B-mode images and Doppler images) from the B-mode data and the Doppler data. The image generating unit 314 associates the generated ultrasonic images with the electrocardiogram and the time information received from the electrocardiographic equipment 360 and stores them in the image memory 315.

The image memory 315 stores therein image data such as a contrast image and a tissue image generated by the image generating unit 314. The image memory 315 also stores therein output signals just passed through the transmitting and receiving unit 311, i.e., radio frequency (RF), the brightness signals of the images, various types of raw data, and image data acquired through a network as necessary. The data format of the image data stored in the image memory 315 may be a data format after being converted into a video format to be displayed on the monitor 340 by the control unit 316, which will be described below, or a data format before being converted into coordinates, which is raw data generated by the B-mode processing unit 312 and the Doppler processing unit 313.

The control unit 316 controls the overall processing performed on the ultrasound diagnosis apparatus 300. Specifically, the control unit 316 controls various types of processing performed by the transmitting and receiving unit 311, the B-mode processing unit 312, the Doppler processing unit 313, and the image generating unit 314 based on various types of setting demands input by an operator through the input device 330, various types of control programs and various types of setting information retrieved from the internal storage unit 317. The control unit 316 also controls the monitor 340 to display thereon the ultrasonic images stored in the image memory 315. The control unit 316 transmits and receives three-dimensional image data (volume data) acquired by other modalities (e.g., an X-ray CT apparatus, an MRI apparatus) through a network according to the digital imaging and communications in medicine (DICOM) standard, for example.

The internal storage unit 317 stores therein control programs for transmitting and receiving the ultrasonic wave, and for image processing and display processing, and various types of data such as diagnosis information (e.g., patient IDs, observations by a doctor) and a diagnosis protocol. The internal storage unit 317 is also used for storing the images stored in the image memory 315 as necessary.

The interface unit 318 is an interface that controls exchanging various types of information between the input device 330, a control device 353, and the apparatus main body 310. The interface unit 318 controls transfer of the positional information acquired by the control device 353 to the control unit 316.

The volume data processing unit 319 executes various types of processing relating to strain analysis. Specifically, through a 3D wall motion tracking technology, an image is generated in which excitation propagation in the heart is drawn. The ultrasound diagnosis apparatus 300 according to the first embodiment here firstly generates the volume data of the heart of the subject P. For example, the ultrasound diagnosis apparatus 300 according to the first embodiment generates a plurality of pieces of volume data (a volume data group) by radiographing the left ventricle (LV) of the heart of the subject P along time series during a period of one or more heartbeats.

The volume data processing unit 319 generates motion information on the motion of the core wall, from each piece of the volume data group along time series generated by scanning the heart of the subject P three-dimensionally with the ultrasound. Specifically, the volume data processing unit 319 generates motion information by pattern matching between the pieces of the volume data. More specifically, the volume data processing unit 319 tracks the tracking points that have been set in a cardiac muscle tissue drawn in each piece of the volume data based on speckle patterns, thereby calculating motion vectors of the respective tracking points. The volume data processing unit 319 then uses the motion vectors of the respective tracking points, thereby generating motion information that represents the motion of a local cardiac muscle. In other words, the volume data processing unit 319 performs three-dimensional speckle tracking and generates motion information. For example, the volume data processing unit 319 generates the local area change rate in the cardiac tissue as motion information.

Figure 4:
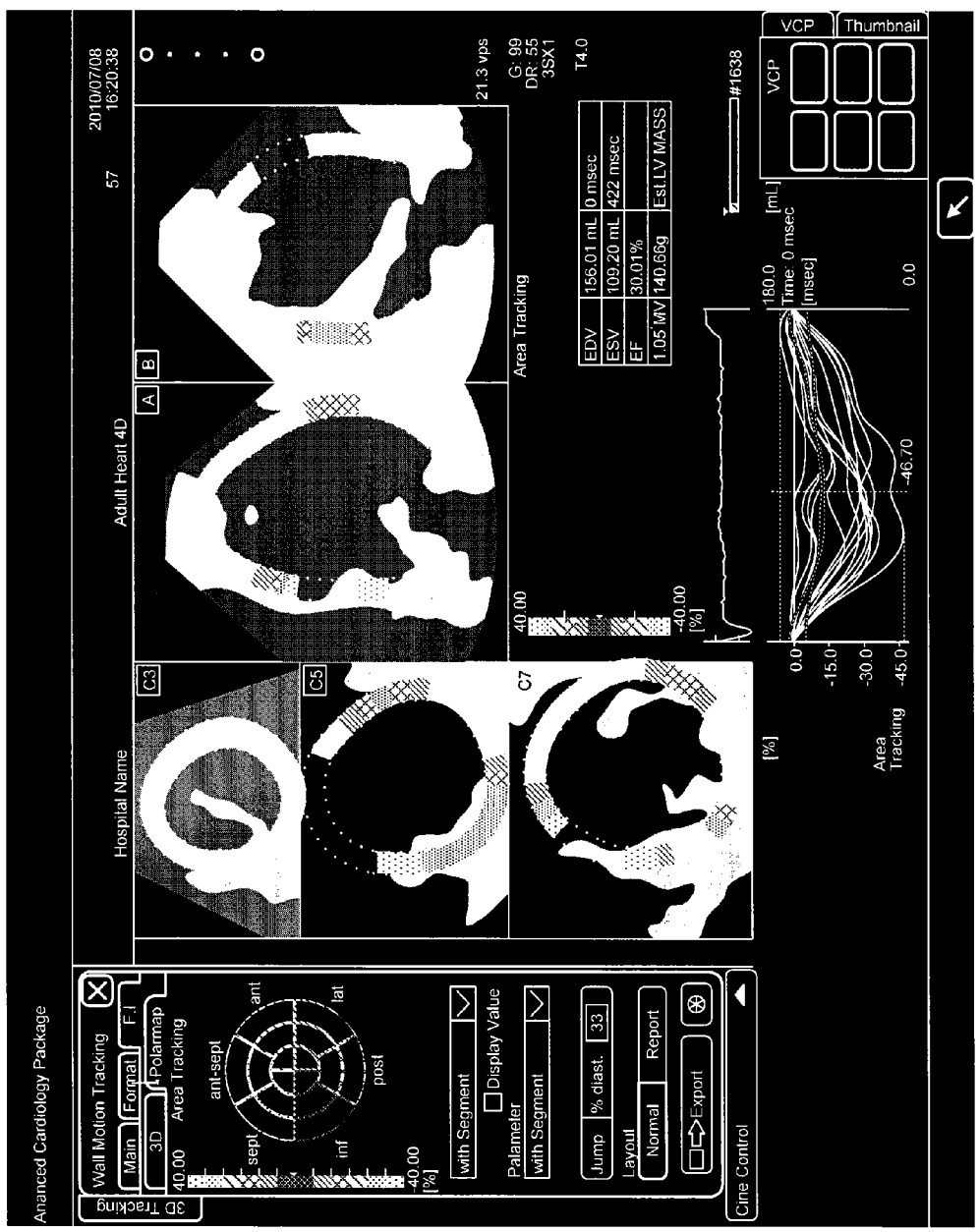
FIG. 4 is a diagram illustrating an example of processing results obtained by a volume data processing unit according to the first embodiment.

FIG. 4 is a diagram illustrating an example of processing results obtained by the volume data processing unit 319 according to the first embodiment. For example, the volume data processing unit 319 can generate a superimposed image in which a specific area is superimposed onto a polar map image through a "time phase holding display method" as illustrated on the left side of FIG. 4. In FIG. 4, "ant-sept" refers to "anteroseptal", "ant" refers to an anterior wall, "lat" refers to a lateral wall, "post" refers to a posterior wall, "inf" refers to an inferior wall, and "sept" refers to "septum".

The volume data processing unit 319 can compose an image from an electrocardiogram and a graph of time change curves of the average motion information (average changing rate of area) for 16 fractions in addition to the time phase holding superimposed image, as illustrated on the bottom in FIG. 4. In FIG. 4, time change curves of the average changing rate of area for each of the 16 fractions are represented with solid lines. Actually, however, the volume data processing unit 319 colors the respective time change curves of the average motion information for each of the 16 fractions in respective colors allocated to each fraction so that it can be understood which time change curve of the average motion information corresponds to which fractions.

The volume data processing unit 319 also generates a plurality of MPR images with a cross section having a short axis or with a cross section having a longitudinal axis from the volume data. In the example illustrated in FIG. 4, the volume data processing unit 319 generates a composite image in the area A. In composite image, a superimposed image including images of a specific area superimposed through the time phase holding method is disposed on the left ventricular core-wall in an apical four-chamber image. In addition, in the example illustrated in FIG. 4, the volume data processing unit 319 generates a composite image in the area B. In composite image, a superimposed image including images of a specific area superimposed through the time phase holding method is disposed on the left ventricular core-wall in an apical two-chamber image.

Furthermore, in the example illustrated in FIG. 4, the volume data processing unit 319 generates a composite image in the area C3. In composite image, a superimposed image including images of a specific area superimposed through the time phase holding method is disposed on the left ventricular core-wall in the image with a cross section having a short axis in the vicinity of the apex. Still furthermore, in the example illustrated in FIG. 4, the volume data processing unit 319 generates a composite image in the area C5. In composite image, a superimposed image including images of a specific area superimposed through the time phase holding method is disposed on the left ventricular core-wall of an image with a cross section having a short axis located between the apex and the base. Still furthermore, in the example illustrated in FIG. 4, the volume data processing unit 319 generates a composite image in the area C7. In the composite image, a superimposed image including images of a specific area superimposed through the time phase holding method is disposed on the left ventricular core-wall in the image with a cross section having a short axis in the vicinity of the base.

In the example illustrated in FIG. 4, together with a color bar and the electrocardiogram, values of various types of motion information are provided as a table. The EDV illustrated in FIG. 4 refers to the volume of the cardiac lumen in the time phase of an end diastole (ED). In the example illustrated in FIG. 4, the EDV indicates "156.01 mL" and the time of the end diastole (reference time phase) indicates "0 msec". The ESV illustrated in FIG. 4 refers to the volume of the cardiac lumen in the time phase of an end systole (ES). In the example illustrated in FIG. 4, the ESV indicates "109.20 mL" and the time of the end systole indicates "422 msec".

The EF illustrated in FIG. 4 refers to the ejection fraction determined from the EDV and the ESV. In the example illustrated in FIG. 4, the EF indicates "30.01%". "1.05×MV" illustrated in FIG. 4 refers to the "cardiac mass (g)" obtained by multiplying the cardiac muscle volume (MV) by the average value of the density of cardiac muscle "1.05 g/mL". In the example illustrated in FIG. 4, "1.05×MV" indicates "140.66 g". Furthermore, in the example illustrated in FIG. 4, "est.LV MASS" is represented, which indicates that the value "140.66 g" is estimated from the cardiac muscle volume of the left ventricle.

Figure 5A:
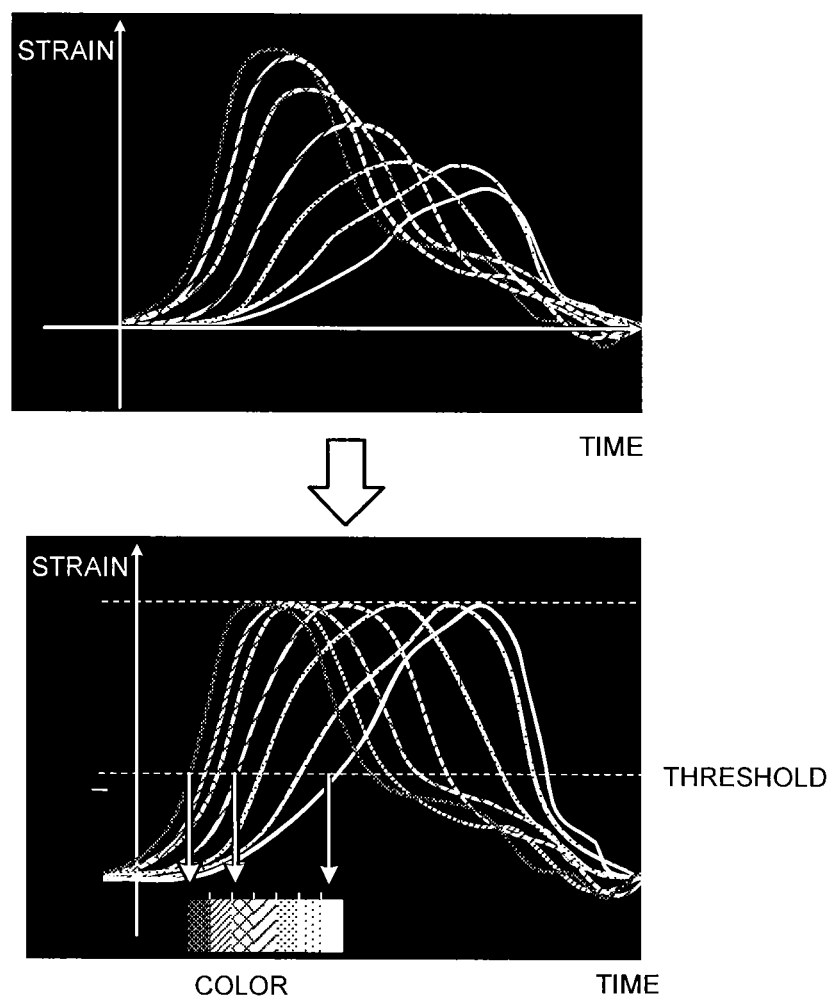
FIG. 5A is a diagram illustrating an example of processing performed by the volume data processing unit according to the first embodiment.

The volume data processing unit 319 may calculate the time change rate (referred to as an "area change rate") of the change in a local area (referred to as a "local area change") as the motion information. That is, the volume data processing unit 319 may calculate the area change rate of the changing rate of area by estimating the time differential value of the local area change. On this occasion, the volume data processing unit 319 changes the color tones of the superimposed image as illustrated in FIG. 5A, by allocating a color for each predetermined threshold time. FIG. 5A is a diagram for explaining an example of processing performed by the volume data processing unit 319 according to the first embodiment.

Figure 5B:
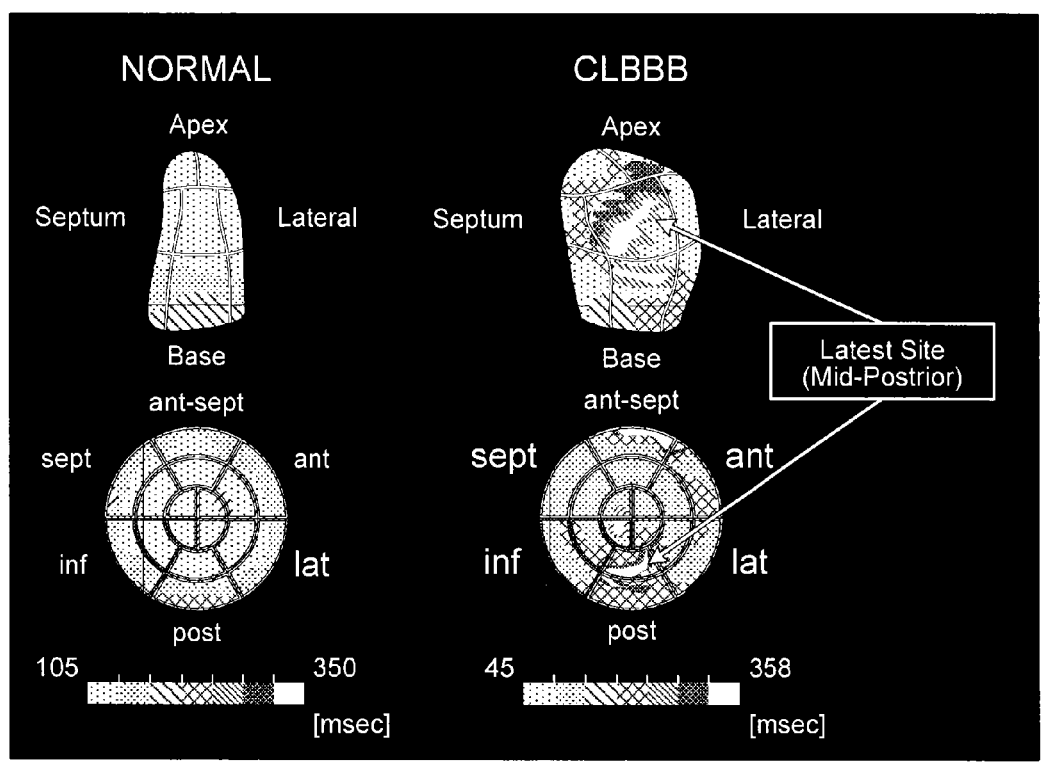
FIG. 5B is a diagram illustrating an example of images generated by the volume data processing unit according to the first embodiment.

FIG. 5B is a diagram illustrating an example of images generated by the volume data processing unit 319 according to the first embodiment. FIG. 5B illustrates the images in which some aspects of excitation propagation in the heart are drawn. Specifically, two following types of superimposed images are illustrated for both an aspect of normal (NORMAL) and an aspect of complete left bundle branch block (CLBBB) in FIG. 5B: the superimposed image color tones are superimposed onto the surface rendering images; and the superimposed image color tones are superimposed onto the polar map images. In the images for CLBBB, sites of latest activation are represented.

In the CRT, the site of latest activation is determined from the superimposed image as illustrated in FIG. 5B, then an electrode (a pacing lead) is placed on the closest vein to the site of latest activation, with reference to an X-ray image obtained by using a contrast material. On this occasion, however, the position of the site of latest activation is not accurately represented in the X-ray image. A doctor may therefore perform manipulation trusting his/her own intuition, resulting in placing the electrode in a wrong position. To avoid this, an ultrasound superimposed image is further superimposed onto the site of latest activation in the X-ray image, thereby helping the doctor to place the electrode in the correct position. On this occasion, the X-ray image and ultrasonic image for the superposition may be a moving image or a still image.

The image processing apparatus 100 according to the present embodiment generates an superimposed image of the X-ray image and the ultrasonic image with the combination of a moving image and a moving image, the combination of a moving image and a still image, or the combination of a still image and a moving image depending on the display state of the images. This achieves displaying a superimposed image of the X-ray image and ultrasonic image with high visibility. The superimposed image of the X-ray image and the ultrasonic image is referred to as a fused image.

Figure 6:
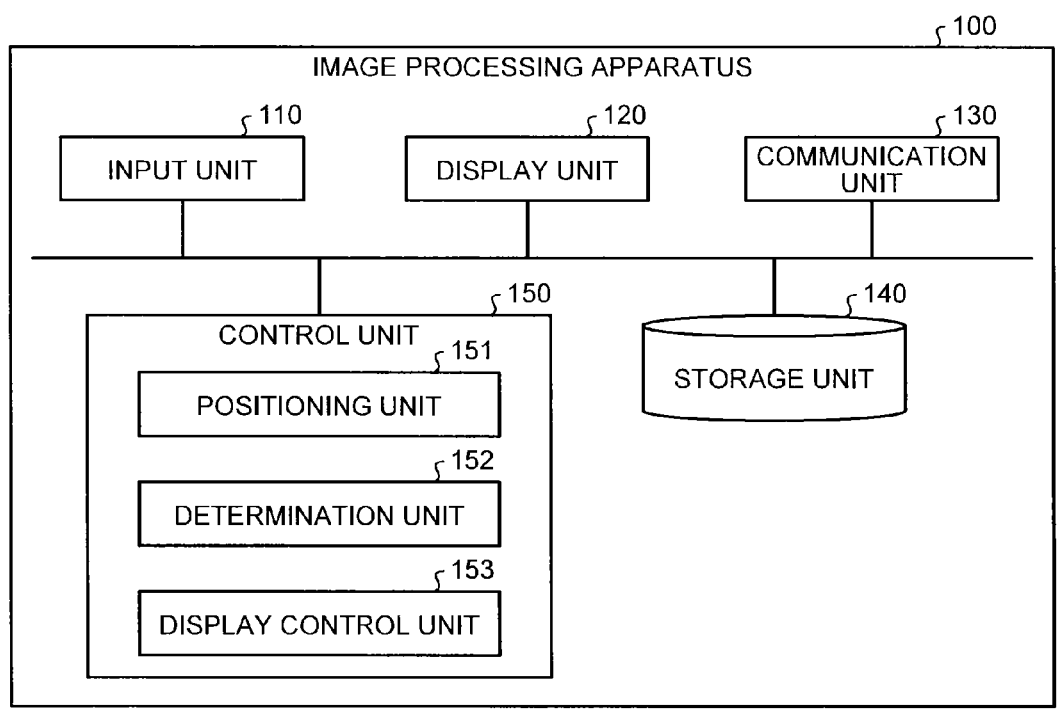
FIG. 6 is a diagram illustrating an example of the configuration of an image processing apparatus according to the first embodiment.

FIG. 6 is a diagram illustrating an example of the configuration of the image processing apparatus 100 according to the first embodiment. As illustrated in FIG. 6, the image processing apparatus 100 includes an input unit 110, a display unit 120, a communication unit 130, a storage unit 140, and a control unit 150. For example, the image processing apparatus 100 is a workstation or a personal computer. The image processing apparatus 100 is coupled to the X-ray diagnosis apparatus 200, the ultrasound diagnosis apparatus 300, and the image storage device 400 through a network.

The input unit 110 is a mouse, a keyboard, or a trackball and receives the input of various types of operations from an operator (e.g., an interpretation doctor) to the image processing apparatus 100. Specifically, the input unit 110 receives an input of information for acquiring an X-ray image or an ultrasonic image.

The display unit 120 is a liquid crystal panel as a monitor, for example, and displays various types of information. Specifically, the display unit 120 displays a graphical user interface (GUI) used for receiving various types of operations from the operator and a superimposed image of the X-ray image and the ultrasonic image that are processing results performed by the control unit 150, which will be described later. The communication unit 130 is a network interface card (NIC), for example, and communicates with another device.

The storage unit 140 is, for example, a semiconductor memory device such as a random access memory (RAM) and a flash memory, or a storage device such as a hard disc and an optical disc. The storage unit 140 stores therein X-ray images and ultrasonic images, for example.

The control unit 150 is, for example, an electronic circuit such as a central processing unit (CPU) and a micro processing unit (MPU), or an integrated circuit such as an application specific integrated circuit (ASIC) and a field programmable gate array (FPGA) and controls the image processing apparatus 100 overall.

Figure 7:
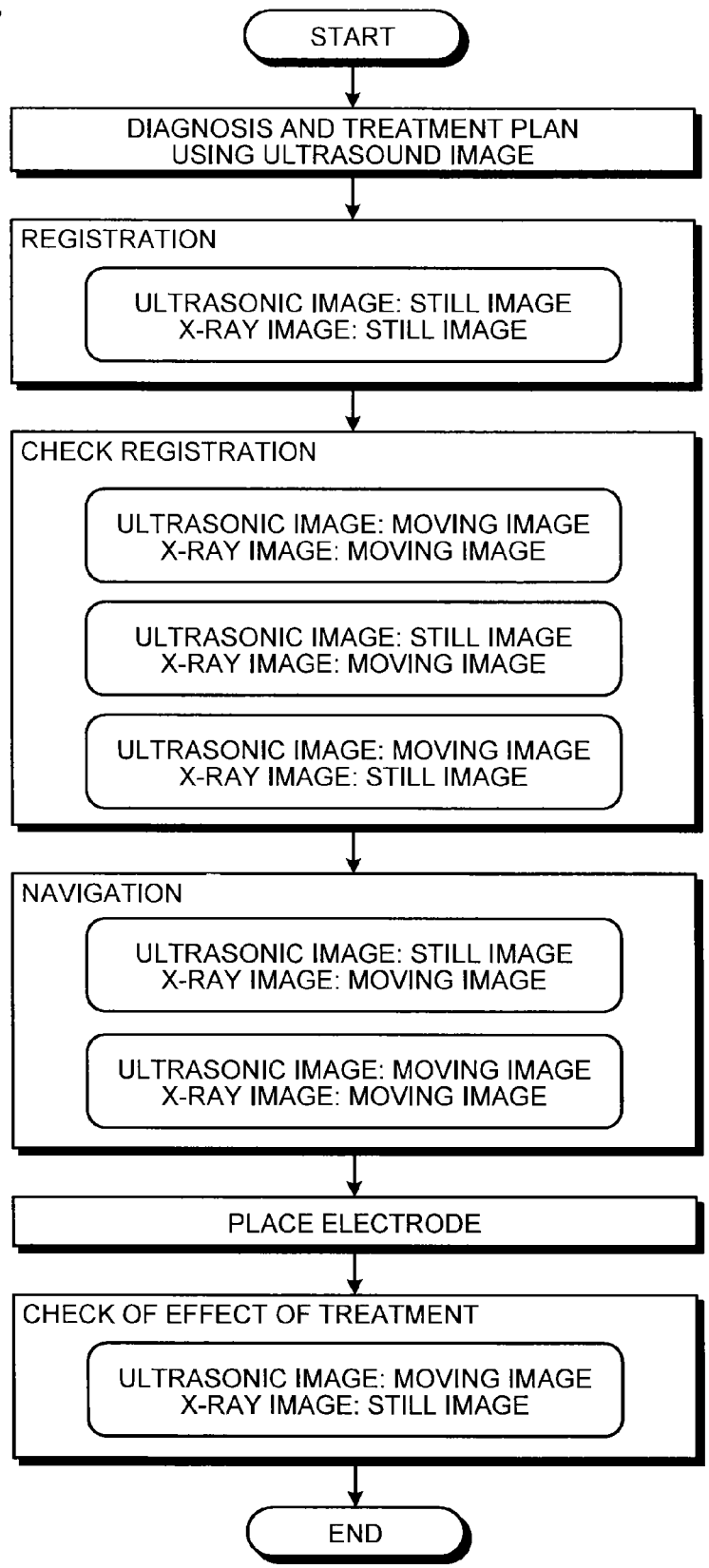
FIG. 7 is a diagram for explaining an example of the display state of fused images according to the first embodiment.

As illustrated in FIG. 6, the control unit 150 includes a positioning unit 151, a determination unit 152, and a display control unit 153, for example. The control unit 150 displays fused images with high visibility by changing the combination of the images used for the fused image depending on the display state of images. First, an example will be described of the display state according to the first embodiment. FIG. 7 is a diagram for explaining an example of the display state of fused images according to the first embodiment. FIG. 7 illustrates a workflow for the manipulation of the CRT.

For example, in the CRT, an ultrasonic image of a heart is acquired by the ultrasound diagnosis apparatus 300 and a diagnosis and treatment plan is developed as illustrated in FIG. 7. In the CRT according to the first embodiment, alignment is performed for the superimposition at the correct position (also referred to as registration). In the fused image here, for example, a still image for an ultrasonic image is superimposed onto a still image for an X-ray image as illustrated in FIG. 7.

In the CRT, for example, it is determined whether the registration is correct (confirmation of the registration). In the fused image here, for example, the combination of the ultrasonic image and the X-ray image is a moving image and a moving image, a still image and a moving image, or a moving image and a still image, as illustrated in FIG. 7. By replaying the moving X-ray image while watching the still ultrasonic image, replaying the moving ultrasonic image while watching the still X-ray image, or replaying both the moving X-ray image and the moving ultrasonic image, an observer such as a doctor checks if the registration is performed correctly.

The doctor then carries an electrode to the closest blood vessel to the site of latest activation while watching the fused image (referred to as navigation), and places the electrode thereon. The fused image here used in the navigation includes a moving X-ray image and a moving or a still ultrasonic image. After that, the effect of the treatment is checked, using a fused image including a moving ultrasonic image and a still X-ray image.

The control unit 150 according to the first embodiment determines the combination of the images included in the fused image depending on the display state as illustrated in FIG. 7. The control unit 150 then displays the fused image of the determined combination on the display unit 120. The display states illustrated in FIG. 7 are only examples. That is, the embodiment is not limited to the example of displaying fused images relating to the manipulation in the CRT. The combinations the images included in the fused image illustrated in FIG. 7 are only examples, and the embodiment is not limited thereto. For example, in the check of the effect of the treatment, another fused image may be used including a moving ultrasonic image superimposed onto a moving X-ray image. The display state and the combination of the images included in the fused image may be determined at the discretion of the observer such as a doctor.

With reference to FIG. 6 again, the positioning unit 151 performs the registration for superimposing an X-ray image and a second image. The positioning unit 151, for example, associates an X-ray coordinate system with an ultrasound coordinate system from the relative positional relation therebetween. The X-ray coordinate system represents an X-ray image with the coordinates in a space where the X-ray image is radiographed, whereas the ultrasonic coordinate system represents an ultrasonic image with the coordinates in a space where the ultrasonic image is captured. FIG. 8 is a diagram for explaining an example of processing performed by a positioning unit 151 according to the first embodiment.

For example, the positioning unit 151 determines the position of the ultrasound coordinate system in the X-ray coordinate system as illustrated in FIG. 8. That is, the positioning unit 151 determines where in the X-ray coordinate system the space ultrasonic images are acquired is located. Examples of registration methods performed by the positioning unit 151 here include the following three methods.

A first method adopts a position sensor. For example, the ultrasound probe 320 having the position sensor 352 is radiographed by the X-ray diagnosis apparatus 200. The positioning unit 151 then calculates the coordinates of the ultrasound probe 320 in the X-ray coordinate system from the position of the ultrasound probe 320 included in the radiographed X-ray image. Subsequently, the positioning unit 151 acquires the positional information of the position sensor 352 when the X-ray image is radiographed from the ultrasound diagnosis apparatus 300. That is, the positioning unit 151 acquires the coordinates of the ultrasound probe 320 in the ultrasound coordinate system when the X-ray image is radiographed.

The positioning unit 151 associates the coordinates of the ultrasound probe 320 in the X-ray coordinate system with the coordinates of the ultrasound probe 320 in the ultrasound coordinate system when the X-ray image is radiographed, thereby determining the position of the ultrasound coordinate system in the X-ray coordinate system. This enables the positioning unit 151 to calculate the coordinates of the determined position of the treatment location using the ultrasonic image in the X-ray coordinate system.

A second method adopts a landmark. For example, an observer sets a landmark in an ultrasonic image for a certain part that can be checked in an X-ray image. The positioning unit 151 registers the ultrasonic image with the X-ray image using the landmark set in the ultrasonic image and the position corresponding to the landmark in the X-ray image. For example, a wall of a ventricle in the ultrasonic image is set as a landmark. The positioning unit 151 registers the X-ray coordinate system with the ultrasound coordinate system using the enhanced X-ray image and the ultrasonic image in which the landmark is set.

A third method adopts a computed tomography (CT) image. For example, the positioning unit 151 registers an ultrasonic image with a CT image, thereby locating the ultrasound coordinate system in the CT coordinate system. The positioning unit 151 registers the X-ray image with the CT image, thereby locating the X-ray coordinate system in the CT coordinate system. The positioning unit 151 then locates the ultrasound coordinate system in the X-ray coordinate system using the position of the ultrasound coordinate system in the CT coordinate system, and the position of the X-ray coordinate system in the CT coordinate system.

As described above, the positioning unit 151 locates the ultrasound coordinate system in the X-ray coordinate system, thereby correctly calculating where the position of the treatment determined in the ultrasonic image is located in the X-ray image. This achieves generating a fused image in which images are superimposed at the correct position. It should be noted that the registration methods as described above are only examples, and the embodiment is not limited thereto. That is, any other method can be used as long as the ultrasound coordinate system can be located in the X-ray coordinate system.

With reference to FIG. 6 again, the determination unit 152 determines whether an X-ray image as a first image is to be displayed as a moving image or a still image, and whether a second image is to be displayed as a moving image or a still image, based on the display state of the images. For example, the determination unit 152 determines the combination of a moving image or a still image of the X-ray image and the ultrasonic image for the fused image according to the workflow illustrated in FIG. 7.

The determination unit 152 here may determine a more detailed combination of the X-ray image and the ultrasonic image for the fused image in addition to the combination of a moving image and a still image. FIG. 9 is a diagram illustrating an example of combinations of images included in a fused image determined by the determination unit 152 according to the first embodiment.

For example, as illustrated in FIG. 9, the determination unit 152 determines the combination of a still image (plus frame-by-frame playback) and a still image (a contrast image) of the ultrasonic image and the X-ray image. This combination of images is set so as to be used mainly at the registration. The X-ray image is a still image in which a blood vessel is enhanced and the ultrasonic image is a still image in which registration information such as a landmark is represented. The ultrasonic image may be an image capable of being played back frame-by-frame.

The determination unit 152 determines, as illustrated in FIG. 9, the combination of a moving image and a still image (a contrast image) of the ultrasonic image and the X-ray image. This combination of images is set so as to be used mainly at the confirmation of the registration. The X-ray image is a still image in which a blood vessel is enhanced and the ultrasonic image is a moving image in which registration information such as a landmark is represented.

The determination unit 152 determines, as illustrated in FIG. 9, the combination of a still image (activation imaging, AI) and a moving image (fluoroscopy or a road map, RM) of the ultrasonic image and the X-ray image. This combination of images is set so as to be used mainly for carrying an electrode, for example. The X-ray image is a moving image of fluoroscopy with which a moving electrode can be guided in real time. The ultrasonic image is a still image on which the planned position for placing an electrode is specified. The X-ray image may be a road map image having blood vessels represented with mask images. The mask image of a blood vessel in the road map image may be a still image or a moving image.

The determination unit 152 determines, as illustrated in FIG. 9, the combination of a moving image (heart rate motion, electrical conduction) and a moving image (fluoroscopy or RM) as the combination of the ultrasonic image and the X-ray image. This combination of images is set so as to be used mainly for carrying an electrode, for example. The X-ray image is a moving image of fluoroscopy with which a moving electrode can be guided in real time. The ultrasonic image is a moving image on which the planned position for placing an electrode is specified and the motion and the electrical conduction of the heart is represented (a moving image with a motion mapped in colors). The X-ray image may be a road map image having blood vessels represented with mask images. The mask image of a blood vessel in the road map image may be a still image or a moving image.

The determination unit 152 determines, as illustrated in FIG. 9, the combination of a moving image (the heart rate motion only) and a moving image (fluoroscopy or RM) as the combination of the ultrasonic image and the X-ray image. This combination of images is set so as to be used mainly for carrying an electrode, for example. The X-ray image is a moving image of fluoroscopy with which a moving electrode can be guided in real time. The ultrasonic image is a moving image on which the planned position for placing an electrode is specified and the motion and the electrical conduction of the heart is represented. The X-ray image may be a road map image having blood vessels represented with mask images. The mask image of a blood vessel in the road map image may be a still image or a moving image.

The determination unit 152 determines, as illustrated in FIG. 9, the combination of a moving image (the electrical conduction only) and a moving image (fluoroscopy or RM) of the ultrasonic image and the X-ray image. This combination of images is set so as to be used mainly for carrying an electrode, for example. The X-ray image is a moving image of fluoroscopy with which a moving electrode can be guided in real time. The ultrasonic image is a moving image on which the planned position for placing an electrode is specified and only the electrical conduction is represented. That is, in the ultrasonic image, the heart rate motion makes no change and only a color map changes. This achieves representing the heart rate motion only in the X-ray image, thereby displaying images with high visibility. The X-ray image may be a road map image having blood vessels represented with mask images. The mask image of a blood vessel in the road map image may be a still image or a moving image.

The determination unit 152 determines, as illustrated in FIG. 9, the combination of a moving image (another window) and a moving image (fluoroscopy or RM) of the ultrasonic image and the X-ray image. This combination of images is set so as to be used mainly for carrying an electrode, for example. The X-ray image is a moving image of fluoroscopy with which a moving electrode can be guided in real time. An ultrasonic image is superimposed onto the x-ray image, and a planned position for placing an electrode is specified in the ultrasonic image. In the combination, a moving image is displayed, in which the electrical conduction is represented in another window. On this occasion, for example, an image in a different format such as a polar-map image may be displayed, or a two-dimensional ultrasonic image may be displayed as a moving image.

With reference to FIG. 6 again, the display control unit 153 controls the display unit 120 to display thereon any one of the superimposed images of the combination of a moving image and a moving image, the combination of a moving image and a still image, and the combination of a still image and a moving image of the X-ray image and the ultrasonic image, and the paralleled image of any one of the above-described combinations, according to the determination made by the determination unit 152. Specifically, the display control unit 153 controls the display unit 120 to display thereon the fused image of the combination of images determined by the determination unit 152. It should be noted that the display control unit 153 controls the display unit 120 to display thereon the fused image registered (aligned) by the positioning unit 151.

If the superimposed image includes a moving image, the display control unit 153 superimposes the X-ray image and the ultrasonic image by synchronizing the phase of the X-ray image and the phase of the ultrasonic image. More specifically, when using the X-ray images acquired in real time for the superimposed image including a moving image, the display control unit 153 calculates the time from the point of the latest R wave to the present time in an electrocardiogram of the subject, and superimposes the ultrasonic image frame on the phase when the time calculated from the point of the R wave elapses in the ultrasonic image onto the X-ray image frame at the present time.

Figure 10A:
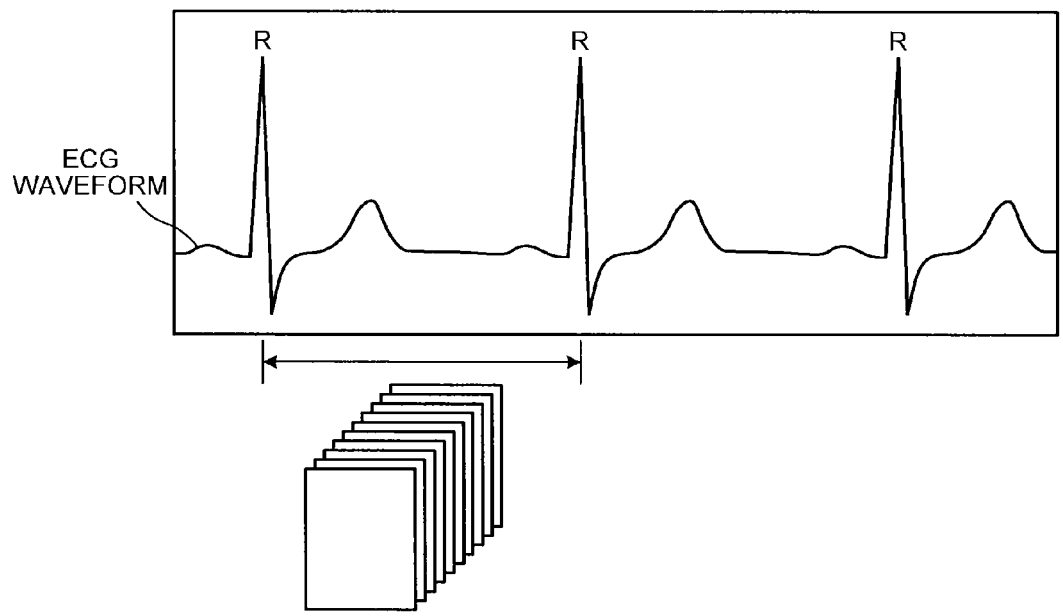
FIG. 10A is a diagram for explaining an ultrasonic image used by a display control unit according to the first embodiment.
Figure 10B:
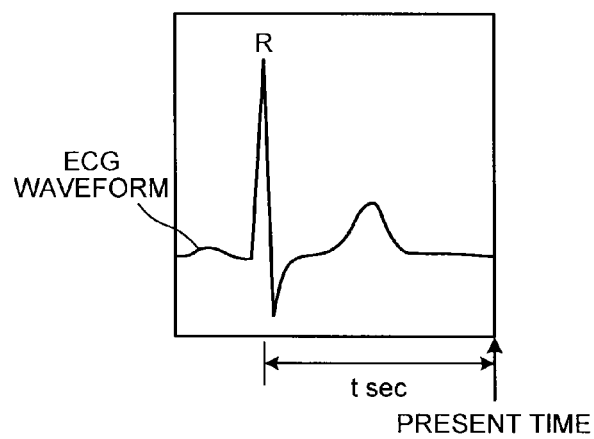
FIG. 10B is a diagram for explaining an X-ray image used for real-time display performed by the display control unit according to the first embodiment.
Figure 10C:
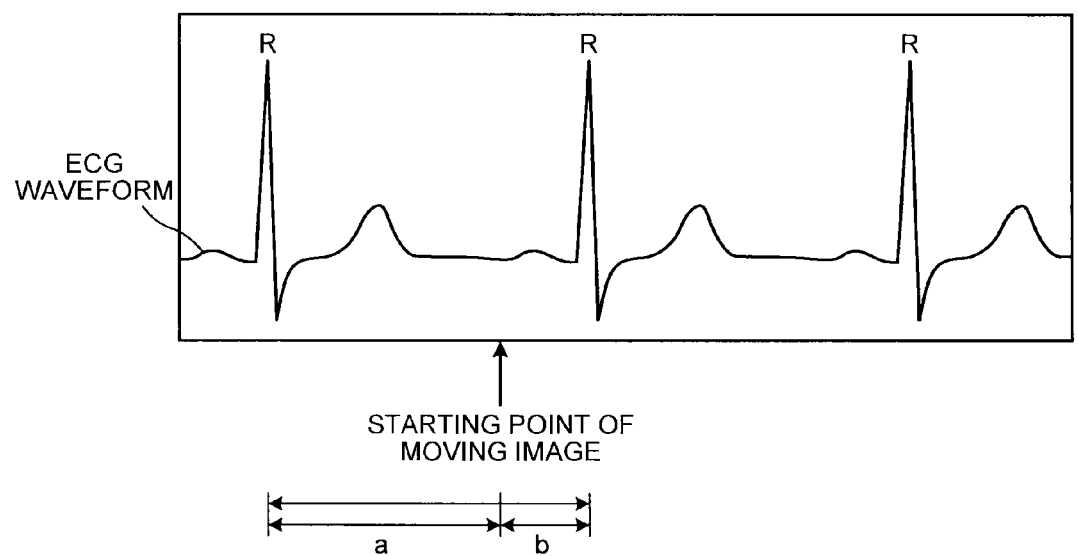
FIG. 10C is a diagram for explaining an ultrasonic image used by the display control unit according to the first embodiment.

The following describes an example in which X-ray images are displayed in real time and ultrasonic images are superimposed onto the X-ray images, with reference to FIGS. 10A and 10B. FIG. 10A is a diagram for explaining an ultrasonic image used by the display control unit 153 according to the first embodiment. FIG. 10B is a diagram for explaining an X-ray image used for real-time display performed by the display control unit 153 according to the first embodiment.

For example, as illustrated in FIG. 10A, the display control unit 153 extracts the frame having almost the same phase as that of the X-ray image at the present time, from the frames of the ultrasonic image acquired during the RR interval of the ECG waveform, and superimposes the extracted frame onto the X-ray image. As illustrated in FIG. 10B, the display control unit 153 acquires the phase corresponding to the frame at the present time of the X-ray image being radiographed in real time from the ECG waveform. That is, the display control unit 153 calculates "t sec", that is, the time from the present time to the latest R wave, as illustrated in FIG. 10B.

The display control unit 153 determines the phase at the time when "t sec" elapses from the R wave out of the frames in the ultrasonic image as the phase almost the same phase as that of the X-ray image at the present time. The display control unit 153 then extracts the frame corresponding to the phase determined from the frames in the ultrasonic image. The display control unit 153 subsequently controls the display unit to display the fused image thereon. In the fused image, the extracted frame of the ultrasonic image is superimposed onto the frame at the present time out of the frames of the X-ray image. It should be noted that the display control unit 153 controls the display unit to display thereon the fused image registered (aligned) by the positioning unit 151. While X-ray images are radiographed in real time, the display control unit 153 determines the phase of the frame of the ultrasonic image having almost the same phase as that of the X-ray image frame at the present time every time an R wave appears on the ECG waveform.

The display control unit 153 calculates the phase of the X-ray image frame in the RR interval of the electrocardiogram of the subject, extracts the ultrasonic image frame having almost the same phase as the calculated phase, and superimposes the extracted ultrasonic image frame onto the X-ray image frame. FIG. 10O is a diagram for explaining an ultrasonic image used by the display control unit 153 according to the first embodiment. FIG. 10O is a diagram for explaining an X-ray image used for display after radiography of the X-ray image ends.

For example, the display control unit 153 calculates, as illustrated in FIG. 10O, where in the RR interval the X-ray image frame at the starting point of the moving image is located. The display control unit 153 extracts the ultrasonic image frame at the position almost the same as the calculated position and then displays the fused image. For example, the display control unit 153 calculates in the RR interval, as illustrated in FIG. 10O, "a:b", that is, the ratio of the period from the starting point of the moving image to the latest R wave to the period from the starting point of the moving image to the immediate subsequent R. The display control unit 153 then extracts the frame having the phase corresponding to the ratio "a:b" in the RR interval in the ultrasonic image. The display control unit 153 controls the display unit 120 to display thereon the fused image in which the extracted ultrasonic image frame is superimposed onto the X-ray image frame at the starting point of the moving image.

The display control unit 153 extracts the X-ray image frame and the ultrasonic image frame having almost the same phase to each other based on the landmark provided on the ultrasonic image and the region in the X-ray image corresponding to the landmark. The display control unit 153 superimposes the extracted X-ray image frame and ultrasonic image frame. Specifically, when the positioning unit 151 registers (aligns) images using the landmark, the display control unit 153 synchronizes the phase of the images using the landmark. For example, the display control unit 153 extracts the frame having almost the same phase as the phase of the frame at the starting point of the moving image out of the ultrasonic image frames based on the position and the shape of the landmark. The display control unit 153 then controls the display unit 120 to display thereon the fused image in which the extracted ultrasonic image frame is superimposed onto the X-ray image frame at the starting point of the moving image.

Figure 11:
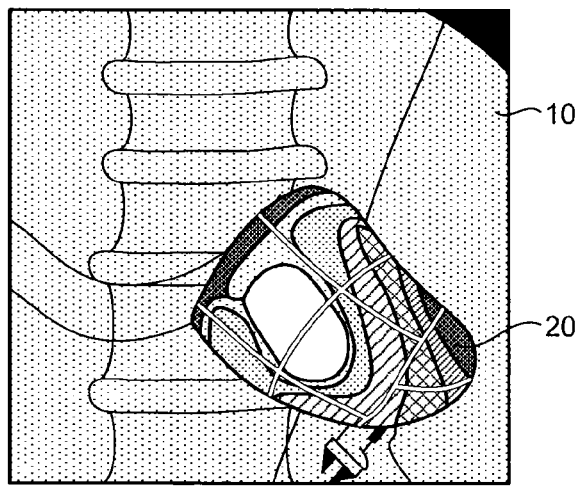
FIG. 11 is a diagram illustrating an example of display control processing performed by the display control unit according to the first embodiment.

FIG. 11 is a diagram illustrating an example of display control processing performed by the display control unit 153 according to the first embodiment. For example, the display control unit 153 controls, as illustrated in FIG. 11, the display unit 120 to display thereon the fused image in which an ultrasonic image 20 (a superimposed image in which color tones are superimposed onto a surface rendering image) onto an X-ray image 10. The display control unit 153 displays the images as a moving image or a still image. When displaying the image as a moving image, the display control unit 153 displays the fused image in which the phase of the images is synchronized.

Figure 12:
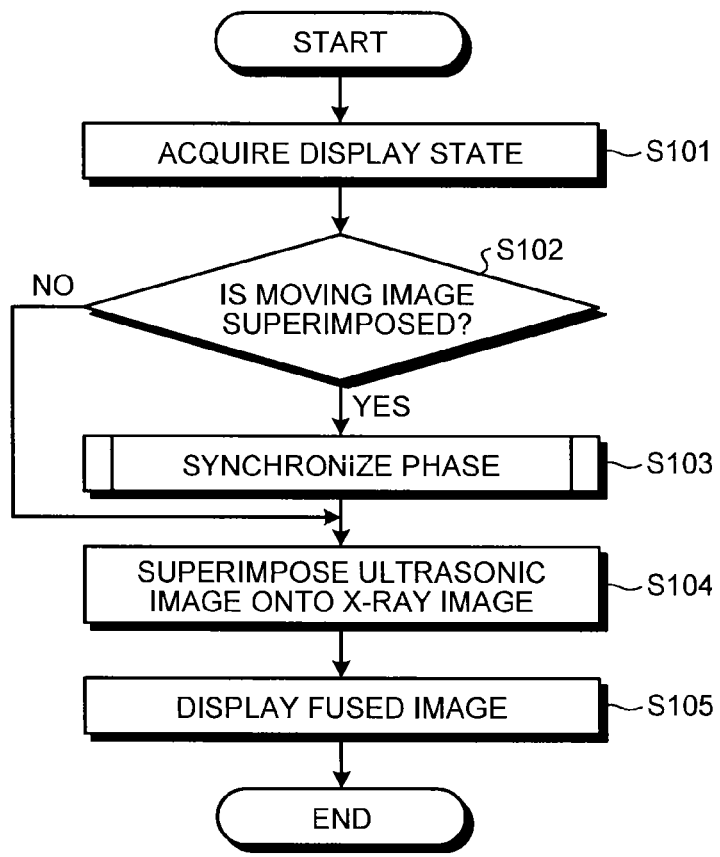
FIG. 12 is a flowchart illustrating procedures for processing performed by the image processing apparatus according to the first embodiment.
Figure 13:
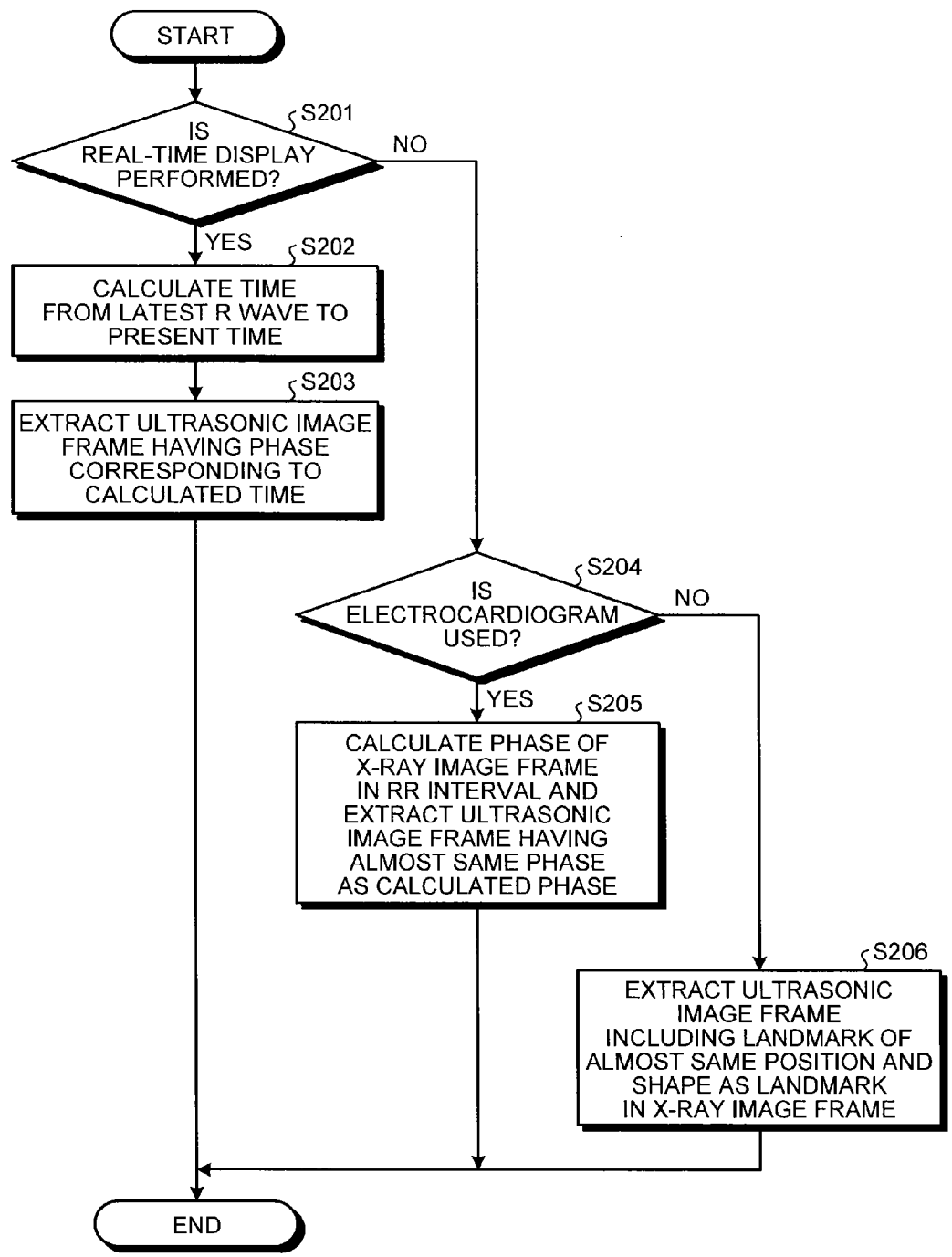
FIG. 13 is a flowchart illustrating procedures for synchronization processing performed by the image processing apparatus according to the first embodiment.

The following describes procedures for processing performed by the image processing apparatus 100 according to the first embodiment. FIG. 12 is a flowchart illustrating procedures for processing performed by the image processing apparatus 100 according to the first embodiment. FIG. 13 is a flowchart illustrating procedures for synchronization processing performed by the image processing apparatus 100 according to the first embodiment. FIG. 12 illustrates the processing after the registration (alignment) processing performed by the positioning unit 151 ends. FIG. 13 illustrates the processing at Step S103 illustrated in FIG. 12 in detail.

As illustrated in FIG. 12, in the image processing apparatus 100 according to the first embodiment, the determination unit 152 acquires the display state (Step S101) and determines whether a moving image is to be superimposed on the image based on the acquired display state (Step S102). If a moving image is to be superimposed on the image (Yes at Step S102), the display control unit 153 synchronizes the phase of the images (Step S103) and superimposes an ultrasonic image onto an X-ray image (Step S104).

If a moving image is not to be superimposed at Step S102 (No at Step S102), the display control unit 153 superimposes an ultrasonic image onto an X-ray image (Step S104). The display control unit 153 controls the display unit 120 to display thereon the fused image in which the ultrasonic image is superimposed onto the X-ray image (Step S105), and the processing ends.

The following describes details on the phase synchronization processing at Step S103. As illustrated in FIG. 13, when synchronizing the phase of the images, the display control unit 153 determines whether real-time display is performed (Step S201). If real-time display is performed (Yes at Step S201), the display control unit 153 calculates the time from the latest R wave to the present time (Step S202). The display control unit 153 extracts the ultrasonic image frame having the phase corresponding to the calculated time (Step S203).

If the real-time display is not performed (No at Step S201) at Step S201, the display control unit 153 determines whether an electrocardiogram is to be used (Step S204). If an electrocardiogram is to be used (Yes at Step S204), the display control unit 153 calculates the phase of the X-ray image frame in the RR interval and extracts the ultrasonic image frame having almost the same phase as the calculated phase (Step S205).

If an electrocardiogram is not to be used at Step S204, (No at Step S204), the display control unit 153 extracts the ultrasonic image frame including the landmark of almost the same position and shape as the landmark in the X-ray image frame (Step S206).

As described above, according to the first embodiment, the determination unit 152 determines which of a moving image or a still image is used for displaying the X-ray image that is a first image and which of a moving image or a still image is used for displaying a second image based on the display state of the images. The display control unit 153 controls the display unit 120 to display thereon the fused image obtained by superimposing any one of the combinations of images: the combination of a moving image and a moving image, the combination of a moving image and a still image, and the combination of a still image and a moving image, of the X-ray image and the second image, according to the determination made by the determination unit 152. This enables the image processing apparatus 100 according to the first embodiment to display a fused image according to the display state of images. In addition, this enables the image processing apparatus 100 to display a superimposed image of an X-ray image and another medical image with high visibility.

According to the first embodiment, if the superimposed image includes a moving image, the display control unit 153 superimposes the X-ray image and the ultrasonic image by synchronizing the phase of the X-ray image and the phase of the ultrasonic image. This enables the image processing apparatus 100 to display an image with high visibility in the manipulation adopting a moving image.

According to the first embodiment, when using the X-ray images acquired in real time to the superimposed image including a moving image, the display control unit 153 calculates the time from the point of the latest R wave to the present time in an electrocardiogram of the subject, and superimposes the ultrasonic image frame on the phase when the calculated time elapses from the R wave in the ultrasonic image onto the X-ray image frame at the present time. This enables the image processing apparatus 100 according to the first embodiment to perform phase synchronization processing on an arhythmia patient on which synchronization is hardly achieved with a simple cardiac synchronization.

According to the first embodiment, the display control unit 153 calculates the phase of the X-ray image frame in the RR interval of the electrocardiogram of the subject, extracts the ultrasonic image frame having almost the same phase as the calculated phase, and superimposes the extracted ultrasonic image frame onto the X-ray image frame. This enables the image processing apparatus 100 according to the first embodiment to readily synchronize the phase.

According to the first embodiment, the display control unit 153 extracts the X-ray image frame and the ultrasonic image frame having almost the same phase to each other based on the landmark provided on the ultrasonic image and the region corresponding to the landmark in the X-ray image. The display control unit 153 superimposes the extracted X-ray image frame and ultrasonic image frame. This enables the image processing apparatus 100 according to the first embodiment to synchronize the phase without acquiring an electrocardiogram.

According to the first embodiment, if the ultrasonic image is mapped in colors, the display control unit 153 reflects the change in the colors on the fused image. This enables the image processing apparatus 100 according to the first embodiment to suppress the reduction of the visibility of the image caused by superimposition of a moving image.

In addition to the first embodiment described above, different embodiments may be achieved.

Figure 14A:
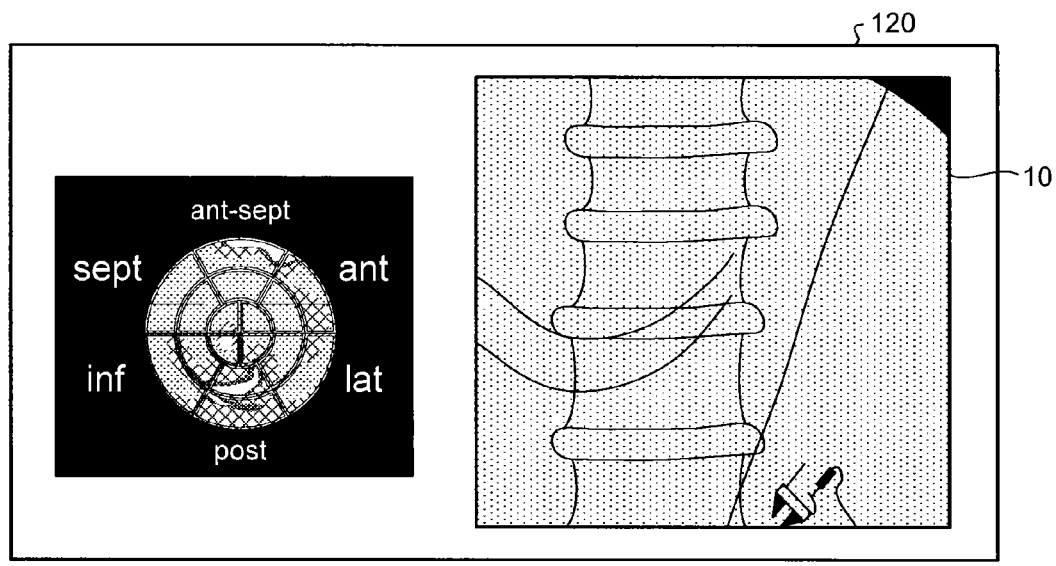
FIG. 14A is a diagram illustrating an example of display control processing performed by a display control unit according to a second embodiment.
Figure 14B:
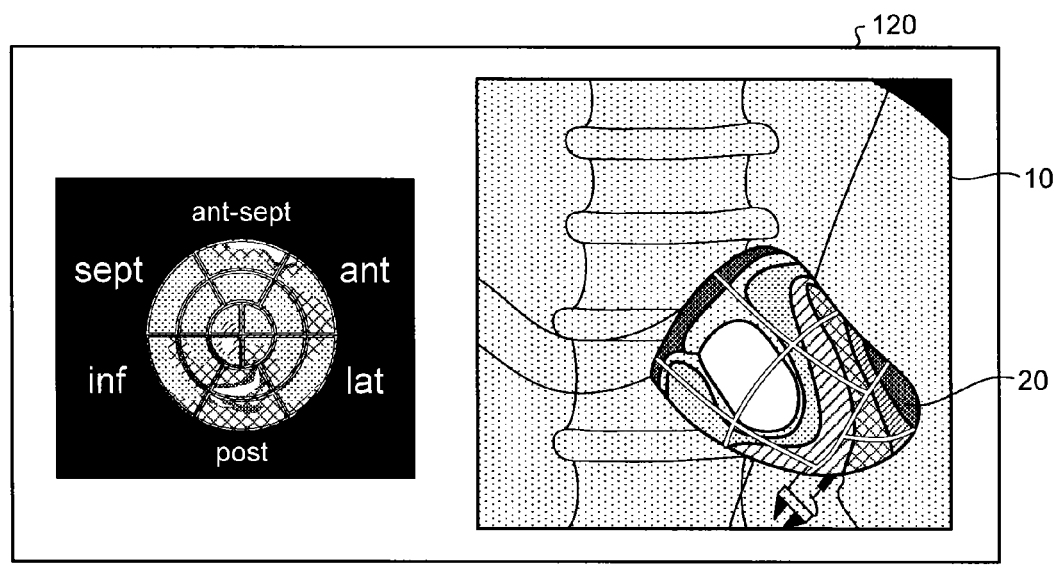
FIG. 14B is a diagram illustrating an example of display control processing performed by the display control unit according to the second embodiment.

In the above-described first embodiment, only a fused image including an ultrasonic image superimposed onto an X-ray image is displayed. However, as described above, the image processing apparatus 100 according to this application is capable of displaying side by side the X-ray image and the ultrasonic image or displaying side by side the fused image and the ultrasonic image. FIG. 14A and FIG. 14B are diagrams illustrating examples of display control processing performed by a display control unit according to a second embodiment.

FIG. 14A illustrates an example of image in which an X-ray image and an ultrasonic image are provided side by side. FIG. 14B illustrates an example of image in which a fused image and an ultrasonic image are provided side by side. For example, a display control unit 153 according to the second embodiment displays side by side in separate windows, as illustrated in FIG. 14A, an X-ray image 10 as a moving image and a polar map image (a moving ultrasonic image) onto which a specific area is superimposed with the time phase holding method. The display control unit 153 displays two moving images by synchronizing the phase therebetween. That is, the display control unit 153 displays two moving images by synchronizing the phase using an ECG waveform, for example, in the same manner as the synchronization method described above.

For example, the display control unit 153 displays side by side in separate windows a fused image in which an ultrasonic image 20 (a superimposed image in which color tones are superimposed onto a surface rendering image) onto the moving X-ray image 10, and a polar map image (a moving ultrasonic image) in which images of a specific area are superimposed through a time phase holding method as illustrated in FIG. 14B. The display control unit 153 displays the fused image and the polar map image by synchronizing the phase therebetween.

In the above-described first embodiment, an ultrasonic image is uses as a second image. The embodiment, however, is not limited to this example. For another example, the following images may be used: a computed tomography (CT) image, a magnetic resonance (MR) image, a positron emission tomography (PET) image, an intravascular ultrasound (IVUS) image, an intracardiac echo (ICE) image, and an electro anatomical mapping (EM) image.

As described above, the image processing apparatus 100 according to this application is capable of displaying side by side the X-ray image and the ultrasonic image in separate windows. This enables the image processing apparatus 100 to provide additional information such as a polar map image in addition to the fused image to an observer.

In the embodiment described above, the image processing apparatus 100 locates the site of latest activation on the X-ray image and superimposes the ultrasonic image on the located position. The embodiment, however, is not limited to this example. For another example, the above-described image processing apparatus 100 is included in an X-ray diagnosis apparatus 200. That is, a system control unit 221 of the X-ray diagnosis apparatus 200 may include the above-described positioning unit 151, the determination unit 152, and the display control unit 153 and perform the above-described processing.

According to an image processing apparatus according to at least one of the embodiments described above, a superimposed image of an X-ray image and another medical image can be displayed with high visibility.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
   a memory configured to store a plurality of combinations of display methods decided for each step of a workflow regarding whether an X-ray image serving as a first image is to be displayed as a moving image or a still image and a second image is to be displayed as a moving image or a still image; and
   processing circuitry configured to
      determine, according to a step of the workflow, a combination of display methods of the X-ray image and the second image from the plurality of combinations of display methods, and
      control a display to display a superimposed image in which the X-ray image and the second image displayed by the determined combination of display methods are superimposed.

2. The image processing apparatus according to claim 1, wherein the second image comprises at least one of an ultrasonic image, a computed tomography (CT) image, a magnetic resonance (MR) image, a positron emission tomography (PET) image, an intravascular ultrasound (IVUS) image, an intracardiac echo (ICE) image, and an electro anatomical mapping (EM) image.

3. The image processing apparatus according to claim 1, wherein when the superimposed image comprises a moving image, the processing circuitry is configured to superimpose the X-ray image and the second image by synchronizing a phase of the X-ray image and a phase of the second image.

4. The image processing apparatus according to claim 3, wherein when using a moving X-ray image acquired in real time for the superimposed image including the moving image, the processing circuitry is configured to calculate a time from a point of a latest R wave to a present time in an electrocardiogram of a subject, and superimpose a frame of the second image of a phase when the calculated time elapses from the point of the R wave in the second image onto a frame of the X-ray image at the present time.

5. The image processing apparatus according to claim 3, wherein the processing circuitry is configured to calculate a phase of an X-ray image frame in an RR interval of an electrocardiogram of a subject, extract a second image frame having almost a same phase as the calculated phase, and superimpose the extracted second image frame onto the X-ray image frame.

6. The image processing apparatus according to claim 3, wherein the processing circuitry is configured to extract an X-ray image frame and a second image frame having almost a same phase to each other based on a landmark provided on the second image and a region corresponding to the landmark in the X-ray image, and superimpose the extracted X-ray image frame and second image frame.

7. The image processing apparatus according to claim 3, wherein when the second image is mapped in colors, the processing circuitry is configured to reflect only changes in the colors on the superimposed image.

8. An X-ray diagnosis apparatus comprising:
 a memory configured to store a plurality of combinations of display methods decided for each step of a workflow regarding whether an X-ray image serving as a first image is to be displayed as a moving image or a still image and a second image is to be displayed as a moving image or a still image; and
 processing circuitry configured to
  determine, according to a step of the workflow, a combination of display methods of the X-ray image and the second image from the plurality of combinations of display methods, and
  control a display to display a superimposed image in which the X-ray image and the second image displayed by the determined combination of display methods are superimposed.

9. A display method comprising:
 determining, according to a step of a workflow, a combination of display methods of an X-ray image serving as a first image and a second image from a plurality of combinations of display methods decided for each step of the workflow regarding whether the X-ray image is to be displayed as a moving image or a still image and the second image is to be displayed as a moving image or a still image; and
 controlling a display to display a superimposed image in which the X-ray image and the second image displayed by the determined combination of display methods are superimposed.

10. The image processing apparatus according to claim 1, wherein the processing circuitry is configured to control the display to display, along with the superimposed image, a polar map image and a graph of time change curves of average motion information.

\* \* \* \* \*